US006952687B2

(12) United States Patent
Andersen et al.

(10) Patent No.: US 6,952,687 B2
(45) Date of Patent: Oct. 4, 2005

(54) COGNITIVE STATE MACHINE FOR PROSTHETIC SYSTEMS

(75) Inventors: Richard A. Andersen, La Canada, CA (US); Bijan Pesaran, Los Angeles, CA (US); Partha Mitra, Summit, NJ (US); Daniella Meeker, Los Angeles, CA (US); Krishna V. Shenoy, Palo Alto, CA (US); Shiyan Cao, Pasadena, CA (US); Joel W. Burdick, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 215 days.

(21) Appl. No.: 10/193,649

(22) Filed: Jul. 10, 2002

(65) Prior Publication Data

US 2003/0023319 A1 Jan. 30, 2003

Related U.S. Application Data

(60) Provisional application No. 60/304,805, filed on Jul. 10, 2001, and provisional application No. 60/304,842, filed on Jul. 11, 2001.

(51) Int. Cl.[7] ........................... G06F 15/18; G06F 17/00
(52) U.S. Cl. ........................... 706/12; 706/47; 623/24; 623/25
(58) Field of Search .................. 706/12, 47; 623/24, 623/25

(56) References Cited

U.S. PATENT DOCUMENTS

| | | | |
|---|---|---|---|
| 4,314,379 A | 2/1982 | Tanie et al. | 623/25 |
| 4,632,116 A | 12/1986 | Rosen et al. | 607/62 |
| 5,246,463 A | 9/1993 | Giampapa | 623/24 |
| 5,314,495 A | 5/1994 | Kovacs | 623/25 |
| 5,406,957 A | 4/1995 | Tansey | 600/545 |
| 5,687,291 A * | 11/1997 | Smyth | 706/47 |
| 6,216,119 B1 | 4/2001 | Jannarone | 706/26 |
| 6,344,062 B1 | 2/2002 | Abboudi et al. | 623/24 |
| 6,546,378 B1 | 4/2003 | Cook | 706/12 |
| 2002/0103429 A1 | 8/2002 | deCharms | 600/410 |
| 2002/0107454 A1 | 8/2002 | Collura et al. | 600/544 |

OTHER PUBLICATIONS

Cook et al, "Development of a Robotic Device for Facilitating Learning by Children Who Have Severe Disabilities", IEEE Transactions on Neural Systems and Rehabilitation Engineering, Sep. 2002.*

Smith et al., "An Artificial Neural Network Model of Certain Aspects of Fighter Pilot Cognition", IEEE International Conference on Decision Aiding for Complex Systems, Oct. 13–16, 1991.

Takahaski et al., "Neural Network for Human Cognitive State Estimation", IEEE International Conference on Advanced Robotic System and he Real World, Sep. 12–16, 1994.

* cited by examiner

Primary Examiner—George B. Davis
(74) Attorney, Agent, or Firm—Fish & Richardson P.C.

(57) ABSTRACT

A prosthetic system may use a decoder to predict an intended action, such as a reach, from processed signals generated from measured neural activity. The decoder may included a cognitive state machine, which transitions between cognitive states based on transition rules.

50 Claims, 8 Drawing Sheets

FIG. 1

Movement A: 205

Movement B: 210

Movement C: 215

COGNITIVE STATE MACHINE FOR PROSTHETIC SYSTEMS

CROSS-REFERENCE TO RELATED APPLICATIONS

This application claims priority to U.S. Provisional Patent Application Ser. No. 60/304,805, filed Jul. 10, 2001, and to U.S. Provisional Patent Application Ser. No. 60/304,842, filed Jul. 11, 2001.

ORIGIN OF INVENTION

The U.S. Government has certain rights to this invention pursuant to Grant No. MDA972-00-1-0029 awarded by the DARPA, Grant Nos. 1RO1-EY-13337-01 and 1RO1-MH-62528-01 awarded by the National Institute of Health, Grant No. EC-9907396 awarded by the NSF, and Grant No. N00014-01-1-0035 awarded by the ONR.

BACKGROUND

Limb prostheses may operate in response to muscle contractions performed by the user. Some of these prostheses are purely mechanical systems. Other prostheses may incorporate electronic sensors to measure muscle activity and use the measured signals to operate the prosthesis. These types of prostheses may provide only crude control to users that have control over some remaining limb musculature.

Prosthetic devices and other assistive aids that require control over some remaining limb musculature may not be useful for individuals who have suffered from upper spinal cord injury, strokes, and neurodegenerative diseases. Prosthetic devices that operate in response to electrical signals measured by a sensor implanted in the subject's brain are being contemplated for assisting these individuals.

SUMMARY

A prosthetic system may use a decoder to predict an intended action, such as a reach, from processed signals generated from measured neural activity. The decoder may include a cognitive state machine, which transitions between cognitive states based on transition rules.

Mathematically, this corresponds to a state space model for cognitive processes. States may be continuously or discretely valued and may be observable or hidden. The transition rules may be described by a matrix of probabilities.

Classifiers may classify the processed signals into period and direction classifications. The period classifications may correspond to neural/behavioral periods and the direction classifications may correspond to intended directions The state machine may transition between cognitive states in response to receiving certain classifications for a predetermined period of time. For example, for a reach, the state machine may transition between a planning state and a reach state in response to receiving a planning classification for a predetermined period of time, e.g., 500 ms. Other state transition models may additionally require that a direction classification is received for the duration of a planning period and/or that a cognitive "go" signal is received.

The cognitive states in the state transition model may be defined based on observation, hypothesis, and experimentation. The cognitive states may also be developed using mathematical modeling techniques such as hidden Markov modeling techniques.

DETAILED DESCRIPTION

Figure 1:
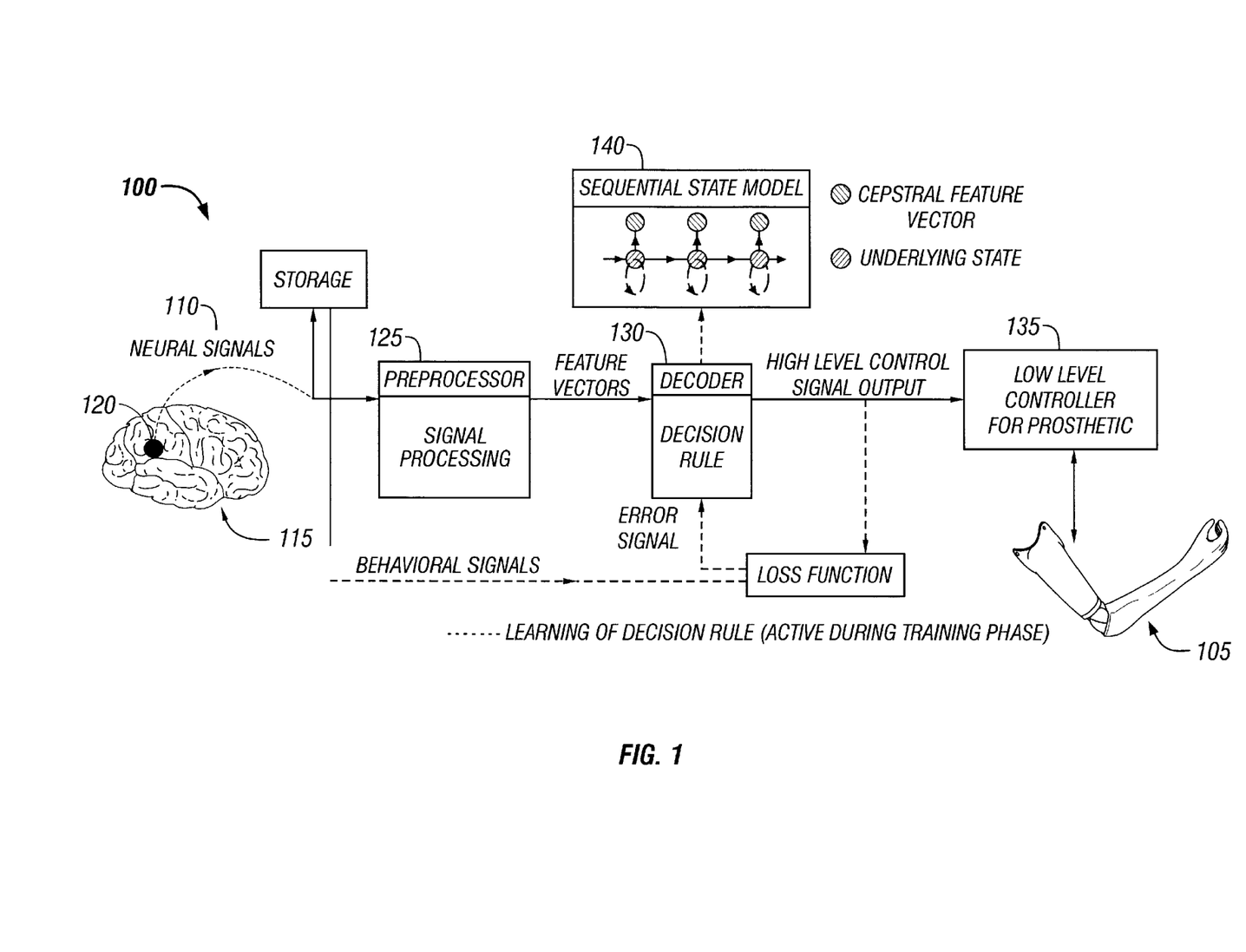
FIG. 1 is a block diagram of a neural prosthetic system including a cognitive state machine.

FIG. 1 illustrates a control system 100 for a prosthetic device 105. Neural signals 110 from a subject's brain 115 may be recorded by a neural implant 120 and transmitted to a preprocessor 125 by a wired or wireless link. The preprocessor 125 may amplify the neural signals 110 received from the implant 120 and transform the signals into a format which facilitates analysis and characterization of the signals. For example, the preprocessor 125 may convert the amplified signals into digital signals and then operate on the signals using digital signal processing techniques, e.g., Fast Fourier Transform (FFT) and spectral analysis operations. A decoder 130 may use the transformed signals to predict an intended movement. The decoder 130 may transmit control signals indicative of the intended movement to a controller 135 for the prosthetic device 105, e.g., a robotic limb.

Figure 2A:
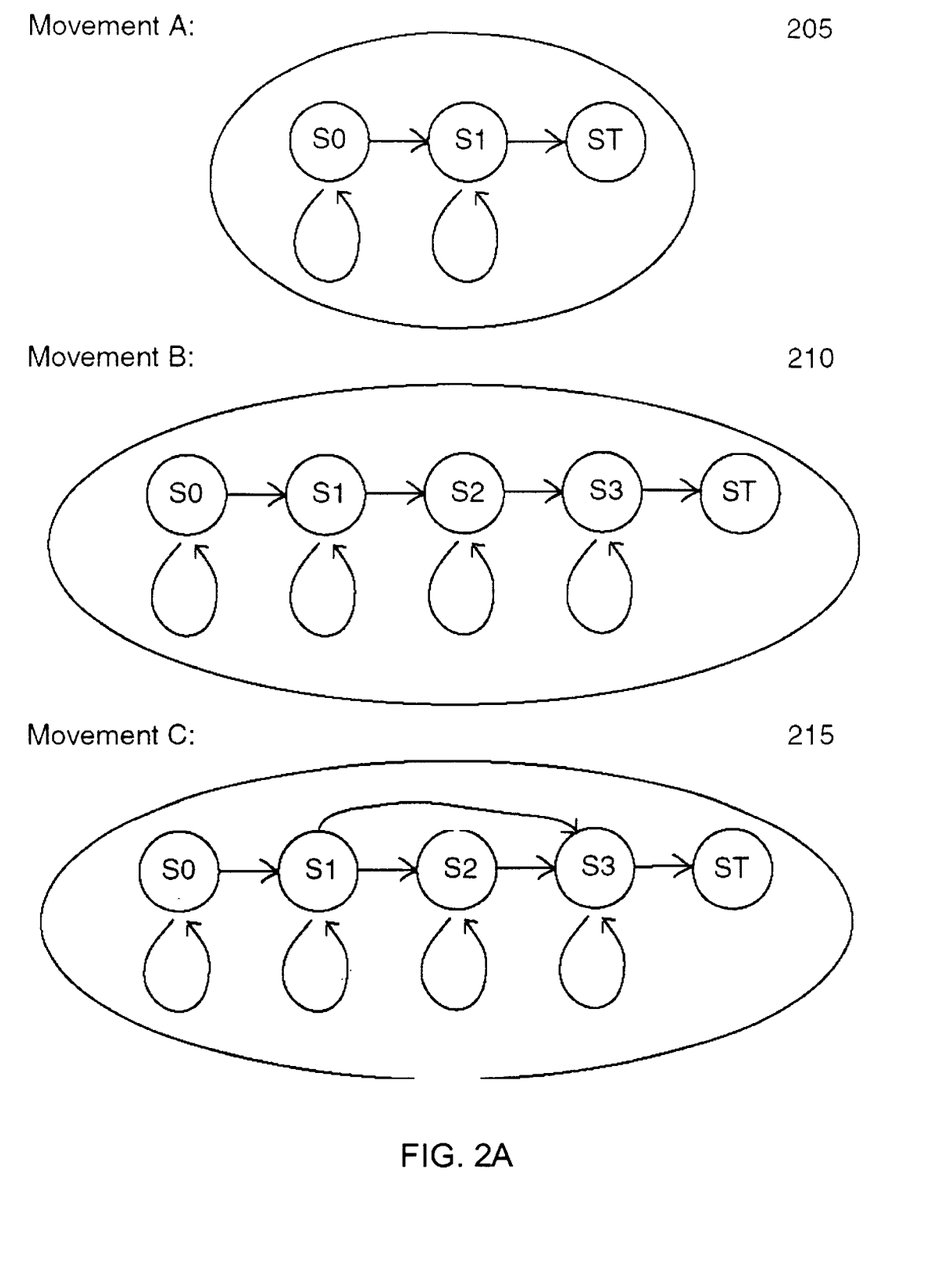
FIG. 2A is a schematic block diagram of a cognitive state model for three movement types.

The neural activity decoded from a subject may transition through different stages between forming an intention to reach and executing the reach. Reach execution may not involve movement of the arm itself, but may involve movement of a virtual arm instead. The decoder 130 may include an interpreter 140 to model the subject's neural activity into states corresponding to these stages, and then use this model to classify transitions between the different states. The interpreter 140 may be implemented as a state machine as shown in FIG. 2A. The states may include, for example, an initialization (or start) state SO, an intermediate state(s) S1, S2, or S3, and a termination state ST. Transitions may be made between states connected by lines with certain probabilities. These transition rules and probabilities may be summarized in a transition matrix.

The interpreter 140 may use different sets of states to construct models of different movements 200. One movement may involve a single intermediate state 205 with all transitions from the start state going through this state before arriving at the termination state. Another movement may involve multiple intermediate states 210 arranged in a left-right order. Additional movements may be modeled by combining these states in different sequences, for example, by changing the transition rules to allow transitions that skip intermediate states 215.

Figure 2B:
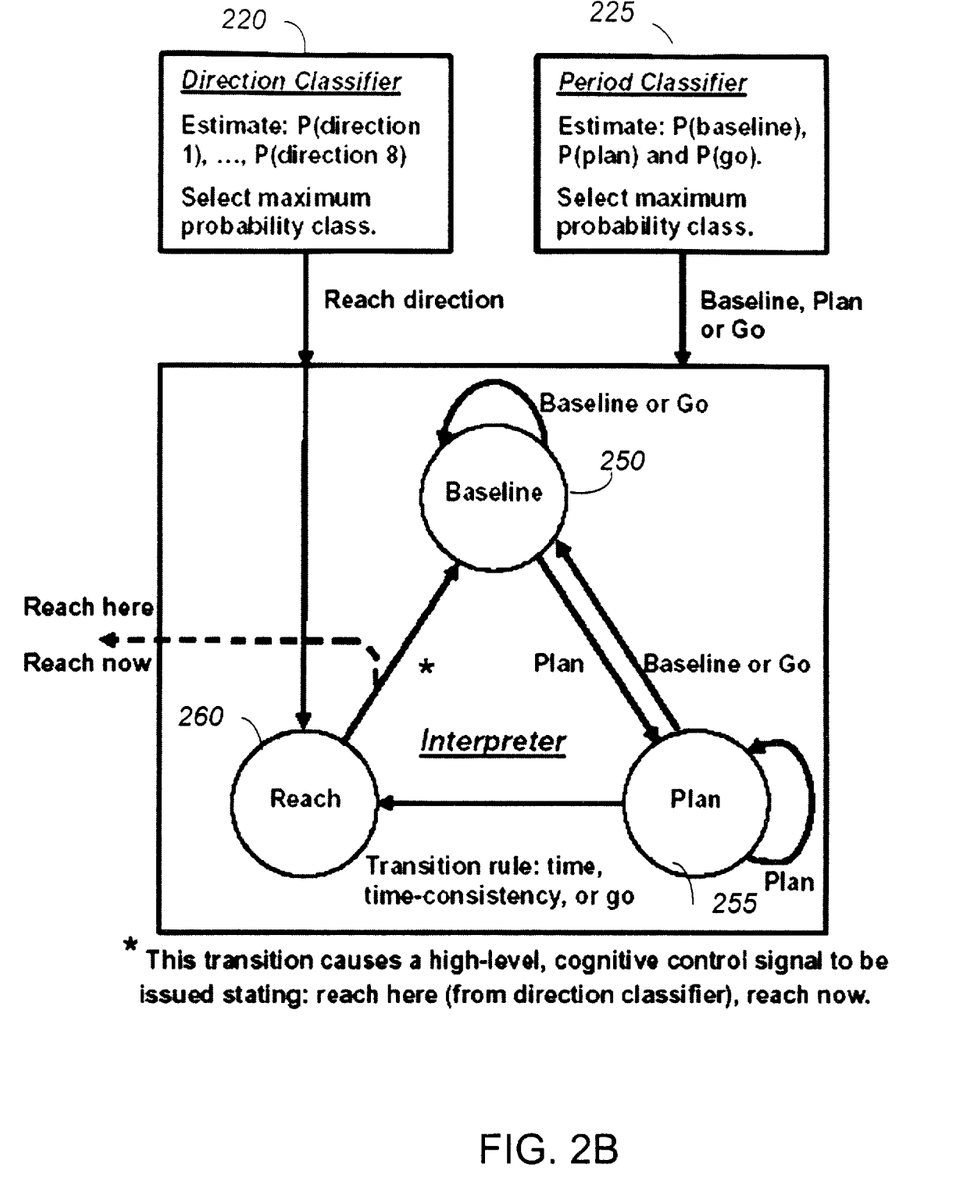
FIG. 2B is a exemplary block diagram of a cognitive state model and decoder.

The interpreter 140 may make transitions between states in response to signals output from state classifiers 220, as shown in FIG. 2B. The classifiers may use neural activity from finite-duration sliding analysis windows to estimate the classifications. The classifiers may calculate the probability of each class at a time slice, and then select the most probable class for subsequent use. When multiple transitions are possible with different probabilities, the classifier may also perform optimizations over different sequences of states to select the class for subsequent use.

EXAMPLE OF A COGNITIVE STATE MACHINE

In an exemplary state machine, the interpreter 140 starts in a baseline state 250 and can transition to a plan state 255 or return to the baseline state 250 each time the period classifier issues another period classification. A baseline or go period classification keeps the interpreter 140 in the baseline state 250, while a plan period classification may advance the interpreter 140 to the plan state 255. Once in the plan state, a baseline- or go-period classification may return the interpreter 140 to the baseline state 250.

The interpreter 140 may use different transition rules to determine when to transition between states. One transition rule may govern transitions from the plan state 255 to the reach state 260, and subsequently trigger an arm movement. A time transition rule may require that the period classifier 225 issue contiguous plan classifications for a minimum period of time, e.g., 500 ms, before transitioning from the plan state 255 to the reach state 260. A time-consistency transition rule may further require that the period classifier's plan classifications specify a given goal direction throughout the required plan period. Alternatively, a "go" transition rule may instead require that the period classifier issue a go period classification, or neural "go signal," after the required plan period.

Once the reach state 260 is achieved, the interpreter 140 may automatically transition back to the baseline state and simultaneously issue a high-level control signal commanding an immediate reach to the location specified by the direction classifier's current estimate. The robotic controller 130 may translate the high-level command signal into a sequence of low-level control signals and use these signals to control the prosthetic device 105 (e.g., robotic limb) to reach in the specified direction. The feedback provided by observing the performance of the prosthetic device 105 may enable the subject to learn to modify neural activity to better operate the control system 100. During training, the loss function 150 in the control system may also be designed to use this feedback to adaptively learn the intended movement. It may do this by comparing the feedback with behavioral instructions 145 given by a training system.

A more sophisticated state machine for modeling reaches may be developed to support more complex behaviors, e.g., tasks requiring precise (prosthetic) hand-eye coordination. Different behaviors may be modeled using state machines with different states and transition rules. The states and transition rules for a state machine, i.e., a state transition model, may be developed through observation, hypothesis, and experimentation. State transition models may also be developed using mathematical modeling techniques.

Hidden Markov modeling is a statistical modeling technique which may be used to develop discrete state transition models with hidden states for use in the interpreter 140. Hidden Markov models (HMMs) have been used in a wide range of applications to infer an underlying, hidden discrete state transition model from a sequence of observations. Generalizations of HMMs not restricted to coupled HMMs, input-output HMMs, artificial neural network/HMM hybrids may be used to develop such models for use in the interpreter 140.

Kalman filtering is a statistical modeling technique which may be used to develop continuous state transition models with hidden states for use in the interpreter 140. Kalman filters have been used in a wide range of applications to infer underlying, hidden continuous state transition models from a sequence of observations. Generalizations of Kalman filters not restricted to nonlinear dynamical systems may be used to develop such models for the interpreter 140.

Powerful tools have been developed which use HMMs to generate state transition models for use in machine learning applications. Such tools may be modified for use in developing cognitive state machines. While the states used in some applications may be truly discrete, the states used in cognitive state modeling may be continuous or discretized for convenience. This may depend on the brain areas used The implant 120 may include an array of electrodes that measure the activity, e.g., spike train activity, of individual cells and the local field potential (LFP) activity of cells in their vicinity. Both types of neural activity may be represented as spectra. The spectra may be computed from small moving windows which capture the temporal information present in both LFPs and spike trains.

The sequence of spectra may be transformed into a sequence of spectral functions, i.e., the cepstrum which is the inverse Fourier transform of the log-spectrum. The sequence of cepstra $c_j$ may be regarded as the observations corresponding to a motor intention $\theta_j$ in a mathematical model. The sequence of cepstra $c_j$ may contain information about both the temporal structure and spike rates through the asymptotic value of the spectrum.

The conditional densities $p(c|\theta)$ may be estimated using either a parametric approach (i.e. Gaussian or mixtures-of-Gaussian densities) or a nonparametric approach (i.e., artificial neural network or a smoothing spline framework see, e.g., Wahba, G., *Spline Models for Observational Data*, Vol. 59 of CBMS-NSF Regional Conference Series in Applied Mathematics, SIAM, Philadelphia, 1990). The transition probability matrix $q(\theta|\theta')$ along with the conditional densities specify the joint distribution of sequences of intended actions and sequences of neural feature vectors. This may be simplified using Markovian independence assumptions to give $$P(c, \theta) = \prod_t p(c_t | \theta_t) q(\theta_t | \theta_{t-1})$$

As described above, the implant 120 may measure the action potential (e.g., spike trains) of single units (SUs) and extracellular potential (e.g., LFP) of cells in their vicinity. In alternate embodiments, the neural activity may be measured in forms other than electrical activity. These include, for example, optical or chemical changes, or changes in blood flow that may be measured by suitable measuring devices.

Figure 3:
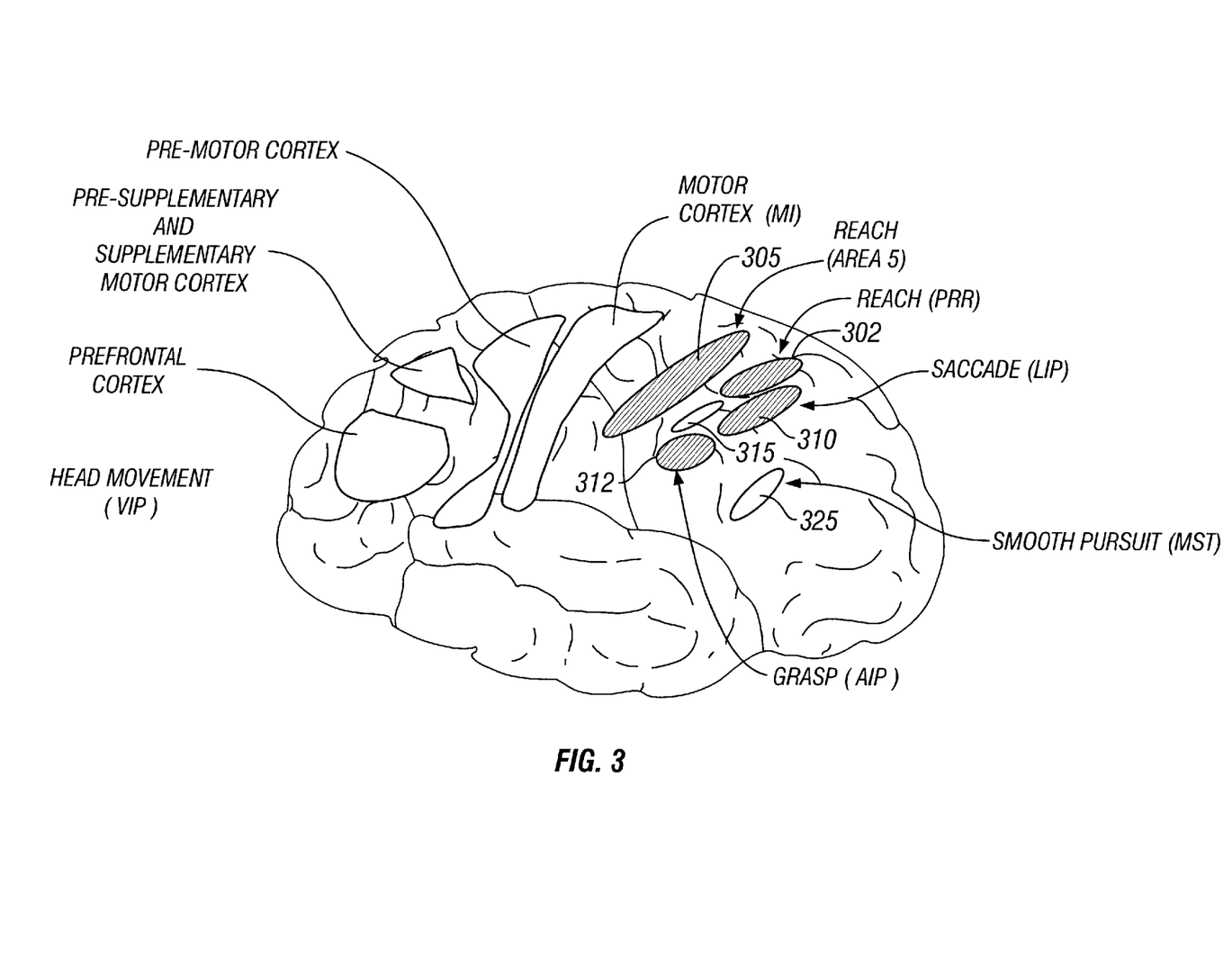
FIG. 3 illustrates potential implant sites for decoding different movements.

FIG. 3 illustrates a number of exemplary implant sites. The implant 120 may be implanted at different sites for decoding different movements. For example, reaches are coded in the parietal reach region (PRR) 302 and area 5 of the superior parietal lobule 305, saccades are encoded in the LIP 310, head movements in the ventral intraparietal (VIP) cortex 315, grasps in the anterior intraparietal (AIP) cortex 320, and smooth pursuit eye movements in the medial superior temporal (MST) cortex 325. Reach and other body movements may be encoded in other areas of the sensory motor cortex. These areas may include, for example, frontal cortical areas involved in movement, such as the motor cortex, ventral and dorsal premotor cortex, supplementary motor area, supplementary eye field, frontal eye field, prefrontal cortex, and pre-supplementary motor area.

The PRR may be a desirable site for a neural implant used to decode reaches. The PRR generates high-level plans for reaching that may require fewer neurons to read out the overall goal of a planned movement than may be required in other areas. PRR neurons code the target of a reach in eye-centered coordinates rather than limb-centered coordinates. Also, the PRR neurons code only the goal of the movement, and appear to code only the next planned movement in a sequential reach task.

The PRR may also undergo less reorganization after acute nerve damage. The removal of an arm or leg or a spinal cord injury may cause grand-scale functional reorganization of cortical maps in both the somatosensory and motor cortices. Since the major input to the PRR appear to be derived from the visual system, which may remain intact in paralyzed patients, the PRR may undergo less reorganization than the somatosensory and motor cortices in these patients.

The measured waveform(s), which may include frequencies in a range having a lower threshold of about 1 Hz and an upper threshold of from 5 kHz to 20 kHz may be filtered as an analog or digital signal into different frequency ranges. For example, the waveform may be filtered into a low frequency range of say 1–20 Hz, a mid frequency range of say 15–200 Hz, which includes the beta (15–25 Hz) and gamma (25–90 Hz) frequency bands, and a high frequency range of about 200 Hz to 1 kHz, which may include unsorted spike activity. The decoder 130 may decode an intended direction using the information in the gamma frequency band (25–90 Hz) of the LFP spectra and the SU spectra. The decoder 130 may decode logical signals using information in the gamma (25–90 Hz) and beta (15–25 Hz) frequency bands of the LFP spectra and the SU spectra. The logical information may include a decision to execute an action, e.g., a "go" signal. The logical information may indicate that the subject is entering other states, such as cuing a location, preparing to execute an action, and scrubbing a planned action.

Experiments and Simulations

Neurophysiological experiments and computer simulations have been performed in our laboratory to demonstrate the proposed state machine architecture for a prosthetic decoder is feasible.

Experiments were conducted on an adult, male Rhesus monkey (*Macaca mulatta*) and, under pentobarbital anesthetic, a head holder and eye coil were implanted. Behavioral training on oculomotor and reaching tasks began no sooner than one week after surgery. The animal received liquid rewards for correct performance during both behavioral-training and experimental sessions. Adequate performance levels, typically well above 90% on all tasks, were achieved after a few months of training.

A second sterile surgical procedure opened a 2 cm diameter craniotomy (right hemisphere, centered on posterior parietal cortex) and implanted a cylinder for chronic access to PRR. Microelectrodes (tungsten with varnish insulation; typically 1–2 Megohms impedance) were advanced at the beginning of each recording session and recorded extracellular action potentials.

The monkey performed three behavioral tasks: a delayed-saccade task, a delayed-reach task, and a coordinate-frame task with four subtasks where eye and initial hand positions varied. Saccades and reaches were made to a vertically oriented 3×4 array of touch-sensitive buttons positioned 24 cm in front of the animal (buttons separated by 180 of visual angle). Each button was 3.7 cm in diameter and contained a red and a green light-emitting diode (LED) behind a translucent window. Delayed-saccade and delayed-reach trials began with illumination of a red and a green LED at the button located straight ahead. The animal would look at and touch this button. A cue was presented (300 ms) at one of the eight locations surrounding the straight-ahead position, 18° or 25.5° from it. A red cue signaled an eventual saccade, and a green cue signaled an eventual reach. After a delay period (800 ms or longer), the central LEDs were extinguished as a "go" signal. The animal then made a saccade or reached to the remembered location of the target. The monkey could not move its hands during saccade trials and had to maintain fixation at the location of the now-extinguished red LED during reach trials. All reaches were performed with the contralateral arm, and the room was completely dark except for the LEDs. Delayed-saccade and delayed-reach trials were interleaved in the first experimental block.

A second experimental block employed the coordinate-frame task, which is a variant of the delayed-reach task. Four subtasks with different eye and initial hand positions were used. In two conditions, the red LED instructing visual fixation was at the button located straight ahead, and the green LED instructing the initial button press was 18° to the left or right. In the other two conditions, the green LED was at the straight-ahead button, and the red LED was 18° to the left or right. The four conditions were otherwise identical to the delayed reach task. For each neuron, the four conditions were pseudorandomly interleaved.

Maximum likelihood estimation, which is equivalent to Bayesian estimation with a uniform prior probability distribution, was used to estimate reach parameters with a cognitive state model using discrete states. Poisson spike statistics and statistical independence between cells were assumed, but explicit models of tuning to the various parameters were not assumed. To reconstruct the planned reach direction, the scalar $x=(1, 2, \ldots, 8)$ was defined to be the reach direction and the vector $n=(n_1, n_2, \ldots, n_N)$ to be the spike count from each neuron ($n_i$) during a time interval (t) Combining the expression for the conditional probability for the number of spikes n to occur given a plan to reach direction x with Bayes' rule yields the following expression for the conditional probability of x given n:

$$P(x|n) = C(\tau, n)P(x)\left(\prod_{i=1}^{N} f_i(x)^{n_i}\right)\exp\left(-\tau\prod_{i=1}^{N} f_i(x)\right)$$

The normalization factor C(t,n) ensures that the sum of the probabilities equals one. P(x) is the prior probability for reaches in each direction, and is uniform by experimental design, and the mean firing rate of the $i^{th}$ neuron while planning a reach to direction x is $f_i(x)$. The estimated reach direction was taken to be the one with the highest probability:

$$\hat{x} = \underset{x \in \{1,2,\ldots 8\}}{\operatorname{argmax}} (P(x|n))$$

Action potentials from 41 PRR neurons from the monkey were analyzed. Cross-validation techniques were used to assess the performance of this estimation process. For each repetition of the simulation, and in each of the eight possible reach directions, a random subset of the total number of cells was selected to avoid a cell sampling bias. One trial was selected randomly, from each of the selected cells, and set aside for use as test data. With the remaining trials from the selected cells, the average firing rates were calculated for each cell while planning to reach to each target. This mean was used as the rate parameter 1 in Poisson distributions.

Figure 4:
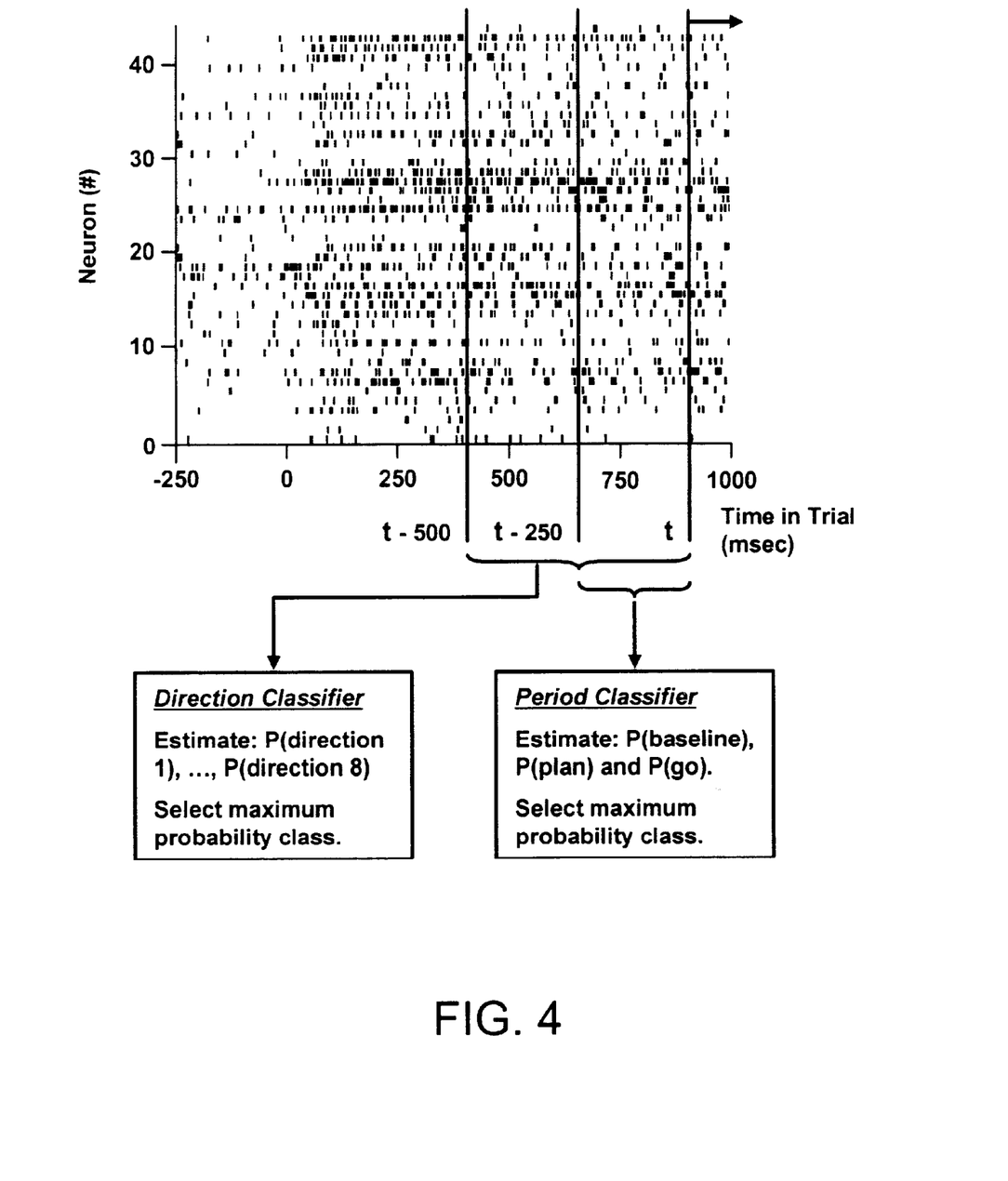
FIG. 4 is a plot showing a spike raster for each of 41 PRR neuron's in a subject as a function of time in a delayed, center-out reach task.

The probability that a particular selection of test data belonged to each of the multidimensional distributions from each direction was assessed, and thus the most probable (i.e., decoded or predicted) reach direction, was selected for each repetition in the given direction. This process was repeated one thousand times in each of the eight reach directions and then normalized to produce the plot in FIG. 4.

A similar procedure was used to estimate the response distributions for the time-course analyses, but with the following variations. After selection of the random subset of cells and the exclusion of a single random trial from each cell, the remaining trials were divided into three epochs: baseline, plan period, and pre-execution period (−600 to 0, 300 to 1000, and 1100 to 1350 msec, respectively). The trials from each direction, for each cell, and in each epoch were concatenated, and the data were sampled with 250 ms long moving windows with 50 ms time steps. The baseline epoch was concatenated across all directions. Additionally the plan epoch was also sampled using 500 ms windows rather than 250 ms windows. The mean of each epoch was used as the parameter for the single multidimensional Poisson distribution for the baseline period, and for each of the eight multidimensional distributions for each direction in the three other epochs (the 250 ms sampled memory epoch, the 500 ms sampled memory epoch and the pre-execution period).

Figure 5:
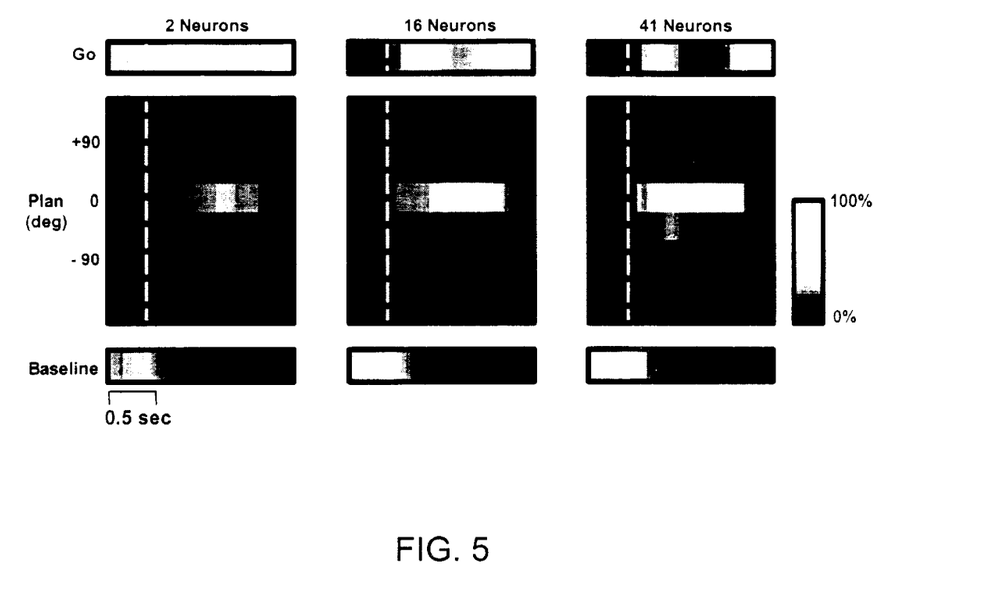
FIG. 5 illustrates classification time courses, averaged over a number of reach goal locations in a behavioral trial for three different neural population sizes.

Test-data firing rates were measured in 250 ms windows, advanced 50 ms at each time step, through the duration of the test trial. The most probable condition (baseline, one of eight plan directions, or one of eight execution directions) was estimated independently in each time step as above. The direct results of this classification process are shown in FIG. 5.

Only cells that had greater average activity while planning reaches than while planning saccades were recorded. While these neurons were thereby deemed reach selective, as opposed to saccade selective, it is still possible that saccade plans could be misinterpreted as reach plans. This idea was tested with the delayed-saccade and delayed-reach data, and estimation techniques, described above. Using all 41 neurons from the monkey, reach plans were never misclassified as saccade plans and only misclassified saccade plans as reach plans in 11.1% of the trials.

To investigate the effect of eye position on PRR activity, spike data (500 ms in the baseline period) were collected for two different initial eye positions (constant hand position). Cross-validation techniques described above were then used to estimate the eye position. We observed that with 2, 4, 8, 16, 32, and more than 32 neurons the correct reconstruction percentages are 74%, 87%, 91.5%, 97.5%, 100%, and 100%, respectively. During the reach plan period, however, this eye position effect was drastically reduced due to the dramatically stronger reach goal location modulation.

Figure 6:
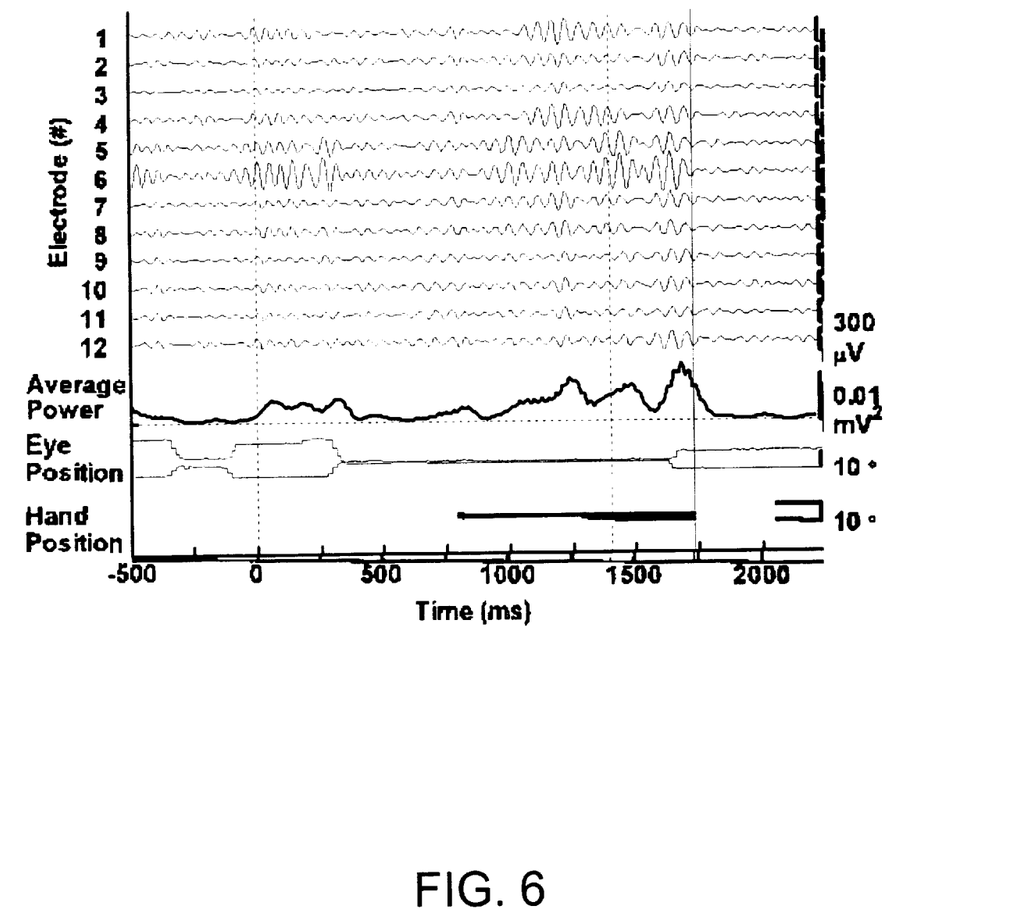
FIG. 6 is a plot showing filtered LFP signals from twelve simultaneously recorded electrodes, along with behavioral traces, for a single behavioral trial.

In another experiment, LFPs were recorded while a monkey looked and reached toward eight peripheral visual targets from a central starting position. A silicon micromachined Utah Electrode Array with 22 active electrodes was implanted permanently within PRR for chronic recording. FIG. 6 shows filtered LFP signals from twelve simultaneously recorded electrodes, along with behavioral traces, for a single behavioral trial. The LFP signals were filtered (15–25 Hz) to retain frequencies well modulated around the time of movement onset, as can be seen in the individual electrode traces and in the average power across electrodes. The average power in this band, and in this trial, is moderate around the time the central fixation and touch targets are illuminated (0 ms), builds just before the peripheral targets specifying the saccade and reach goals become visible (~1400 ms), and declines rapidly around the time of movement onset (~1740 ms). Further examination revealed that power in this band is modulated by both saccadic eye movements and reaching arm movements. Reaching arm movements tend to modulate the power to a greater extent that do saccadic eye movements, with power being reduced to nearly zero directly after reach onsets.

If this power increase just before a movement, followed by a power decrease at or around the time of movement, is stereotyped and robust it should be possible to detect this power signature and use the time of this event to further improve system performance. More specifically, a matched (power) filter could detect from the LFP when a movement is to occur. This LFP-based estimate could be combined with a spike-based estimate of when a movement is to occur, as employed by the go transition rule described previously, and used to form another, higher-performance interpreter 140 transition rule.

Figure 7:
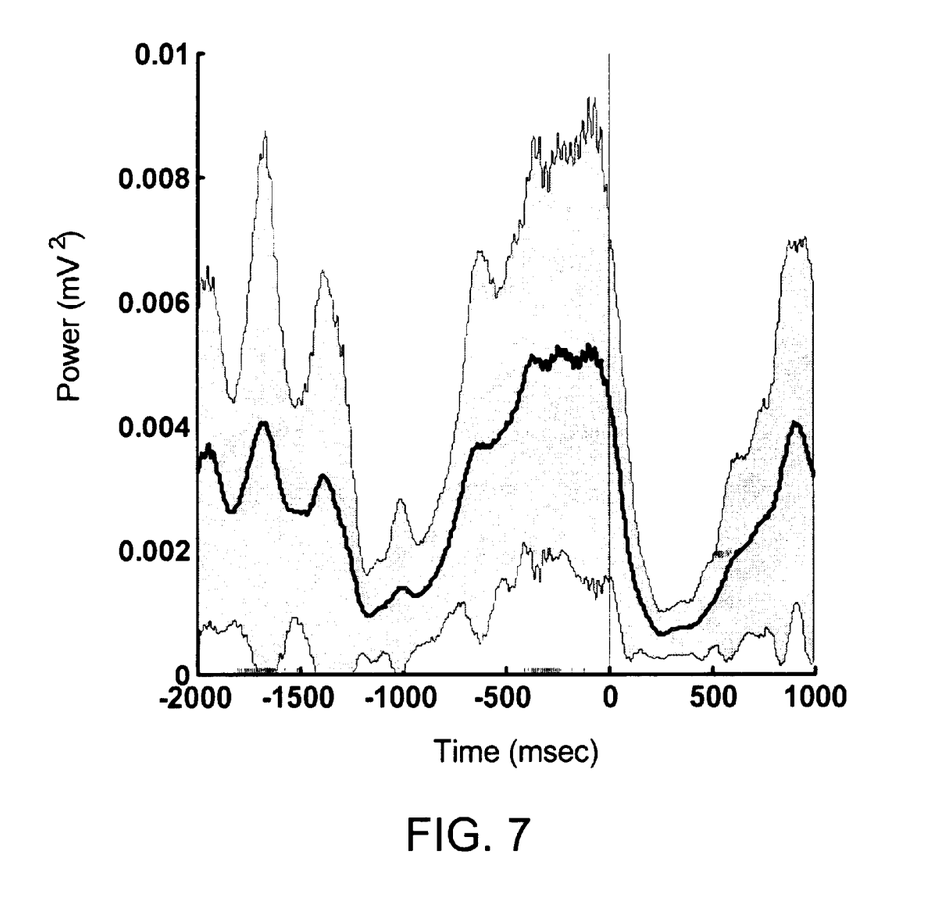
FIG. 7 is a plot showing local field potential (LFP) signals and power (15–25 Hz band) in a center-out movement task.

To assess how stereotyped and robust this power feature is, FIG. 7 plots the 15–25 Hz power averaged across all trials (six repetitions in each of eight directions) and aligned, trial by trial, to reach onset (0 ms). As with the single-trial data trace shown in FIG. 6, the average power begins to build approximately 500 ms before the peripheral target is displayed (~200–400 ms before reach onset), and presumably indicates an anticipatory response resulting from the fixed, and therefore predictable, timing of the peripheral target display. Also consistent with the single trial in FIG. 6, the average power begins to fall precipitously just before the movement begins (0 ms). This rapid decline in power, culminating in a period of near zero power, appears stereotyped and robust.

As described above, the control system 100 may be used to control a prosthetic device 105 such as a robotic limb. The control system 100 may also be used to control a variety of other devices including, for example, muscle stimulators in a natural limb, conveyance means (e.g., a motorized wheelchair), and a pointing device for a personal computer (PC).

A number of embodiments have been described. Nevertheless, it will be understood that various modifications may be made without departing from the spirit and scope of the invention. Accordingly, other embodiments are within the scope of the following claims.

What is claimed is:

1. A method comprising:
   receiving a processed signal generated from measured neural activity;
   transitioning between states in a state sequence in a cognitive state machine in response to said processed signal; and
   generating a command signal indicative of an intended movement corresponding to said state sequence.

2. The method of claim 1, wherein the neural activity comprises single unit activity.

3. The method of claim 1, wherein the neural activity comprises local field potential activity.

4. The method of claim 1, further comprising:
   classifying the processed signal into discretely valued states corresponding to a cognitive state.

5. The method of claim 1, wherein the neural activity comprises a single unit activity and a local field potential activity.

6. The method of claim 1, further comprising:
   classifying the processed signal into continuously valued states corresponding to a cognitive state.

7. The method of claim 1, wherein the states correspond to cognitive states that are observable.

8. The method of claim 1, wherein the states correspond to a cognitive state that are hidden.

9. The method of claim 1, wherein said transitioning comprises transitioning between states according to transition rules.

10. The method of claim 1, wherein said transitioning comprises transitioning between states defined by transition rules described by a transition matrix that determines probabilities.

11. The method of claim 1, wherein said generating comprises generating the command signal from a state sequence according to the optimization of a cost function.

12. The method of claim 1, wherein said generating comprises generating the command signal from a state sequence according to the optimization of a cost function that maximizes expected probability over all sequences.

13. The method of claim 1, wherein said generating comprises generating the command signal from a state sequence according to the optimization of a cost function that minimizes risk over all sequences.

14. The method of claim 1, further comprising:
classifying the processed signal into a period classification.

15. The method of claim 1, further comprising:
classifying the processed signal into a direction classification indicative of an intended direction for said movement.

16. The method of claim 1, wherein said transitioning comprises transitioning from a planning state to a movement state.

17. The method of claim 1, wherein said intended movement comprises a reach.

18. The method of claim 1, wherein said transitioning comprises transitioning between states in response to receiving a classification corresponding to a first state in the sequence for a predetermined time period.

19. The method of claim 1, wherein said transitioning comprises transitioning from a planning state to a movement state in response to receiving a planning classification for a predetermined time period.

20. The method of claim 1, wherein said transitioning comprises transitioning from a planning state to a movement state in response to receiving a planning classification and a direction classification for a predetermined time period.

21. The method of claim 1, wherein said transitioning comprises transitioning from a planning state to a movement state in response to receiving a planning classification for a predetermined time period and a cognitive go signal.

22. A method comprising:
observing neural signals from a subject in a period in which the subject forms an intention to perform a movement;
recording a plurality of observations;
determining a plurality of underlying cognitive states in response to said observations; and
generating a cognitive state transition model including said cognitive states.

23. The method of claim 22, wherein said generating comprises optimizing a mathematical model including said observations using a cost function.

24. The method of claim 22, wherein said determining comprises generating a mathematical model including said observations.

25. The method of claim 22, wherein said observing comprises observing spectra generated from electrical activity measured in a subject's brain.

26. The method of claim 25, wherein said electrical activity comprises spike train activity.

27. The method of claim 25, wherein said electrical activity comprises local field potential activity.

28. The method of claim 25, wherein said observations comprise spectra.

29. The method of claim 25, wherein said observations comprise functions of spectra.

30. Apparatus comprising:
a state machine operative to transition between a plurality of cognitive states in response to signals generated from neural activity, said cognitive states including a termination state; and
a signal generator operative to generate a control signal indicative of an intended movement in response to the state machine transitioning through a state sequence.

31. The apparatus of claim 30, wherein said neural activity comprises single unit activity.

32. The apparatus of claim 30, wherein said neural activity comprises local field potential activity.

33. The apparatus of claim 30, wherein said cognitive states comprise a baseline state and a planning state.

34. The apparatus of claim 30, wherein the cognitive state machine is further operative to transition from the planning state to the movement state in response to receiving signals indicative of a planning period for a predetermined period of time.

35. The apparatus of claim 30, wherein the cognitive state machine is further operative to transition from the planning state to the movement state in response to receiving signals indicative of a planning period and a direction for a predetermined period of time.

36. The apparatus of claim 30, wherein the cognitive state machine is further operative to transition from the planning state to the movement state in response to receiving signals indicative of a planning period for a predetermined period of time and receiving a cognitive go signal.

37. The apparatus of claim 30, further comprising a classifier operative to classify said signals into one of a plurality of classifications.

38. The apparatus of claim 37, wherein the classifier is further operative to select a classification of highest probability from a plurality of classifications.

39. The apparatus of claim 37, wherein said classifications comprise classifications corresponding to cognitive states.

40. The apparatus of claim 37, wherein said classifications comprise classifications corresponding to directions.

41. The apparatus of claim 30, wherein said intended movement comprises a reach.

42. A system comprising:
an implant operative to measure neural activity;
a signal processor operative to transform said measured neural activity into a processed signal;
a decoder operative to predict an intended movement from said processed signal, the decoder including
a state machine operative to transition between a plurality of cognitive states in response to the processed signal, said cognitive states including a termination state;
a signal generator operative to generate a control signal indicative of the intended movement in response to the state machine transitioning through a state sequence; and
a controller operative to control a device to perform a movement corresponding to-the intended movement in response to said control signal.

43. The system of claim 42, wherein the neural activity comprises electrical activity in a subject's brain.

44. The system of claim 42, wherein the device comprises a robotic limb.

45. The system of claim 42, wherein the intended movement comprises an intended reach.

46. An article comprising a machine-readable medium including machine-executable instructions, the instructions operative to cause a machine to:
 receive a processed signal generated from measured neural activity;
 transition between states in a state sequence in a cognitive state machine in response to said processed signal; and
 generate a command signal indicative of an intended movement corresponding to said state sequence.

47. The article of claim 46, wherein the neural activity comprises electrical activity in a subject's brain.

48. The article of claim 46, wherein said transitioning comprises transitioning from a planning state to a movement state.

49. An article comprising a machine-readable medium including machine-executable instructions, the instructions operative to cause a machine to:
 observe neural signals from a subject in a period in which the subject forms an intention to perform a movement and performs the movement;
 record a plurality of observations;
 determine a plurality of underlying cognitive states in response to said observations;
 generate a cognitive state transition model including said cognitive states; and
 determine the control signal corresponding to a said state sequence.

50. The article of claim 49, wherein the instructions operative to cause the machine to observe comprise instructions operative to cause the machine to observe spectra generated from electrical activity measured in a subject's brain.

* * * * *